United States Patent [19]
Hoenninger, III et al.

[11] Patent Number: 5,606,258
[45] Date of Patent: Feb. 25, 1997

[54] CONTROL INTERFACE FOR AN MRI SYSTEM

[75] Inventors: John C. Hoenninger, III, Oakland; Lawrence E. Crooks, Richmond, both of Calif.

[73] Assignee: The Regents of the University of California, Oakland, Calif.

[21] Appl. No.: 32,647

[22] Filed: Mar. 17, 1993

[51] Int. Cl.$^6$ .................................................. G01V 3/00
[52] U.S. Cl. .......................................... 324/309; 324/312
[58] Field of Search .................................. 324/300, 307, 324/309, 310, 311, 312, 314; 364/200, 414

[56] References Cited

U.S. PATENT DOCUMENTS

| | | | |
|---|---|---|---|
| 4,689,564 | 8/1987 | Leve et al. | 324/312 |
| 4,707,661 | 11/1987 | Hoenninger, III et al. | 324/309 |
| 4,764,894 | 8/1988 | Codrington | 324/312 |
| 4,845,613 | 7/1989 | Netter et al. | 364/200 |
| 5,068,786 | 11/1991 | Netter et al. | 324/312 |
| 5,144,242 | 9/1992 | Zeilenga et al. | 324/312 |
| 5,465,361 | 11/1995 | Hoenninger, III | 324/312 |

*Primary Examiner*—Louis M. Arana
*Attorney, Agent, or Firm*—Nixon & Vanderhye P.C.

[57] ABSTRACT

A control interface for a magnetic resonance imaging (MRI) system provides extended, improved linker syntax/techniques that maximize reuse of program segments, allow optimal compromise between detailed representation and efficient sequence program design and maintenance, and permit uniform application of the loop syntax to link commands for MRI sequencers with a wide range of hardware implementations. The control interface provides, among other features, generalized loops at the link level; loop symbols representing loop identity can be associated with scope and/or range (with some kind of limited grammar in the link command itself that supports identification of scope and/or range); parameter tables that can be associated with loop symbols (any given table can be associated with N loop symbols in order to provide multidimensional sequences); multiple levels of loop nesting; and directed limited syntax that provides limited grammar, and range and syntax checking and requires the user to explicitly enter information into the interface.

28 Claims, 6 Drawing Sheets

Fig. 3 LOOP TABLE

Fig. 4 SYMBOL TABLE

CONTROL INTERFACE FOR AN MRI SYSTEM

CROSS-REFERENCES TO RELATED APPLICATIONS

The present invention provides an improvement to the techniques disclosed in commonly-assigned U.S. Pat. No. 4,707,661 to Hoenninger III et al entitled "Machine Generation of Machine-Executable State-Change Instructions for Magnetic Resonance Imaging" (Nov. 17, 1987) ("the '661 patent"). The entire disclosure of the '661 patent is incorporated herein by reference.

The subject application is also related to my copending commonly assigned application Ser. No. 07/579,631 filed Sep. 10, 1990 entitled "FAST LINKER FOR AN MRI SEQUENCER" (atty. ref. 89–179).

FIELD OF THE INVENTION

The present invention relates to magnetic resonance imaging (MRI) systems, and more particularly, to method/apparatus for generating executable code for an MRI sequencer/controller. Still more particularly, the invention relates to a linker and associated generalized linker syntax for efficient machine generation of MRI sequencer instructions.

BACKGROUND AND SUMMARY OF THE INVENTION

My '661 patent discloses an assembler/linker process that utilizes predetermined control program sequences together with program-change tables ("PCTs") of MRI parameter values in order to efficiently machine-replicate MRI-slice-specific instructions for execution by a MRI controller/sequencer. The exemplary technique disclosed in the '661 patent involves defining predetermined slice-specific program segments of machine-executable MRI sequencer instructions so as to reference symbolic addresses and predetermined PCTs. At link time, the program segments are accessed and corresponding symbolic addresses and/or referenced PCT entries are indexed to machine replicate a predetermined set of slice-specific program segments.

For many years now, Diasonics Medical Division (and later Toshiba) has been commercializing a "LSIMON" MRI control program Segment Editor which supports capabilities disclosed in my '661 patent. However, that Segment Editor and associated linker does not support general syntax for program segment arguments, nested loops and loop indices, multi-dimensional sequence parameter lookup tables, and parameter formulas (equations). The LSIMON MRI linker is limited to three loop names (S, R and C) and the use of these loops is restricted. This is especially true of the C index, which can only be used for an outer loop. Also, parameter lookup tables (which were called parameter change tables or "PCTs") would only be associated with either the S or C loop index. A newer version of the MRI Sequence Editor and linker included in the MRIMON program was commercially released more than a year ago. That newer version included a spreadsheet program segment representation but was not enhanced to include the further features disclosed herein since it was initially made to be backward compatible with LSIMON.

While the exemplary linker syntax and associated techniques disclosed in my '661 patent (and incorporated into LSIMON and its later MRIMON version) have been highly successful for development and full scale clinical MRI imaging systems, further improvements are possible. In particular, it would be highly desirable to extend such exemplary linker syntax/techniques so as to increase flexibility and efficiency without sacrificing verifiability and ease of software maintainability/debugging.

The present invention provides extended, improved linker syntax/techniques that maximize reuse of program segments in creating sequence programs, allow optimal compromise between detailed representation and efficient sequence program design and maintenance, and permit uniform application of the loop syntax to link/load commands for MRI sequencers with a wide range of hardware implementations.

The following are among some of the important features of an MRI control interface provided by the present invention:

generalized loops at the link level;

loop index symbols representing loop identity can be associated with scope and/or range (with some kind of limited grammar in the link command itself that supports identification of scope and/or range);

parameter tables can be associated with loop index symbols (any given table can be associated with N loop index symbols in order to provide multidimensional sequences);

any level of loop nesting is possible;

directed limited syntax providing limited grammar and syntax checking, and requiring user to explicitly enter information into the interface.

By way of brief background, MRI sequencer program segment instructions may be regarded as machine states expressed as microcode instructions, with each microcode field corresponding to an entry in the program segment (or procedure) source code. A "procedure" is herein distinguished from a program segment by its property of having arguments passed to it in the link command. An overall programming model provided by the present invention generalizes microcode fields (including PCT entries) to "cells". Such cells may have "properties" or "attributes" such as, for example:

a constant value; or a variable name; or a (globally defined) symbolic procedure argument; or a value specified by a formula; or a value referenced from a PCT; or if the "cell" is part of a PCT entry, it can refer to another PCT (thus allowing indirect PCT access).

These techniques allow the possibility of having only a few program segments or procedures represent single-slice template sequences which support all spin echo or all partial flip or all 3D multi-slice/multi-volume imaging protocols for example—thereby drastically decreasing the total amount of code to be written and maintained.

The control interface provided by the present invention may be a separate (e.g., software) machine that can be interfaced to more than one hardware MRI sequencer and control system. The control interface processes link commands composed of syntax primitives including sequence program segment(s), procedure argument(s) (which may be enclosed by parentheses for example), and delimiters (e.g., curly brackets) indicating the beginning and end of loops and loop index symbols with associated loop index starting and ending values. The segments and/or procedures are program code fragments which are linked together as specified in the link command to create an ordered set of states which are encoded for the MRI sequencer hardware (regardless of its design) to execute. The result is a set of timed MRI system events which allow the creation of a complete MRI data set. Within the program segment(s) it is also possible to define loops for execution which are independent of the loops in the link command and which may reference line symbols in other program segments. A spreadsheet representation may be used for the program editor, with each sequence parameter occupying a cell.

A specific sequence parameter in a spreadsheet cell may be defined to be either fixed, a variable, dependent on a lookup table, or dependent on a formula (equation). In the case of the lookup table, a lookup index is associated with the table. Also, an entry in the lookup table may be fixed, a variable, dependent on another lookup table (this allows multidimensional tables), or on a formula (equation). As the linker creates the set of states for execution by the MRI sequencer, values specified with lookup tables are accessed when needed to set a parameter value by using the current loop index value for the loop symbol associated with that lookup table. In the case of multidimensional lookup tables, nested loops can be used to specify the value of a parameter. The loop syntax provides nesting of loops within multiple sets of curly brackets. Lookup tables can be grouped into sets identified by different levels, as in a 3D spreadsheet, and the link command will use the group of tables for the level specified at the end of the link command and preceded by a semi-colon.

A wide range of sequence coding requirements can be addressed with the broad capabilities of this type of programming model. The more generalized but constrained grammar/syntax also improves the self-documentation of the link commands and decreases the number of different sequences required to support desired sequence protocols. For example, the new techniques permit arguments in the calling specification of the sequence procedure(s) in the link command, and also allow a global system constant (e.g., TR or TE) to be used as an argument with internal derivation of the required parameter value(s) for a given machine state.

The exemplary syntax disclosed in the '661 patent provides only two inner software loops with very restricted usage for slice selection, and a rigid outer loop used for phase encoding. As mentioned above, one of the more salient features of the improved programming model and associated linker loop syntax and linker provided by the present invention is a generalized, more flexible outer loop and the capability for plural nested inner loops with arbitrary loop index symbols that may be used to index N-dimensional PCTs. In the preferred embodiment, the loops are provided at the link level and are used to iteratively generate multiple "copies" (with necessary variable information changed) of object microcode with all addresses resolved for execution by the sequencer.

Thus, the new loop index symbol feature provided by the present invention provides generalized looping at the link level. Loop index symbols represent loop identity. A grammar preferably requires loop index symbols to be explicitly associated with scope and/or range parameters such that the range of loop values is specified in the link command itself. Named loops are explicitly associated with parameter tables (PCTs). PCTs may be referenced by any number (one to N) of loop index symbols to provide nested looping capabilities such that any grammatically correct ordering of loop index symbol/table references can be used. A directed, limited syntax editor may be used to provide range checking and application specific syntax checking in order to enforce a limited grammar that is constrained to the particular MRI application for higher reliability. This is not the case if a commonly available programming language (e.g., C) is used.

Note also that program segments may include variables which require resolution at link time which are either global or passed by value or reference. This means that the program segments become procedures while still retaining the special properties of a program segment embedded in loop control structures which are part of the linker syntax.

One of the advantages of more generalized looping and other associated features provided by the present invention is the ability to accommodate three-dimensional imaging requirements much more efficiently. In the exemplary syntax described in the '661 patent, imaging sequences for three-dimensional imaging require multiple link commands ("P-commands"). In the more generalized syntax provided by the present invention, a new "D" loop enclosing the "C" loop can, for example, be used to specify repetition of the original "P-command." This allows a single linker command to generate slice-direction related instructions for a number of phase encodings with an axis perpendicular to the plane of the phase encoding gradient. A D-type PCT can be used in conjunction with this linker loop, with the D-index being re-evaluated after each complete set of phase encoded projections specified by the "C" loop.

Inner volume imaging has also been difficult to handle in the past since in such cases the 180 degree volume selective irradiation is perpendicular to the thick 90 degree slice selection irradiation which selects the cross-section for 3D phase encoding. The new generalized programming syntax/techniques provided by the present invention can be used to allow separate selection of the delta F frequency to be used for the 180 degree irradiation. The '661 patent discloses the use of an "S-field". In accordance with the more generalized syntax provided by presently preferred exemplary embodiment of the present invention, a second "J" loop may be provided enclosing the "S" loop. The "J" loop may be used to select the offset frequency from a PCT similar to the one used for electronic positioning along the axis of the patient. Such a link command allows for a continuum of TR and TE values through the arguments supplied to the basic sequence procedures combined to create the final sequence, while still providing a one-to-one relationship between the code specified by the link command and the code loaded into the sequencer memory. This one-to-one relationship is important to provide straightforward software verification and hardware debugging.

The preferred embodiment provided by the present invention also provides global definitions of special symbols and procedure arguments. Such global definitions provide various advantages in terms of avoiding duplication of code. For example, globally defined special symbols (e.g., the last letters in the alphabet, "X", "Y", "Z") may be used as entry points (assuming they have not already been encountered by the linker in previous segments). Thus, it becomes possible to provide, for example, a single instance of the entry symbol in the symbol table for the first instruction in the main "S" loop, and this entry symbol can be jumped to directly (thus saving a main routine instruction preceding the "S" loop and reducing the number of sequencer reloads). This is in contrast with the exemplary technique disclosed in the '661 patent, which required a main program segment to provide a jump destination.

BRIEF DESCRIPTION OF THE DRAWINGS

These and other features and advantages of the present invention will be better and more completely understood by referring to the following detailed description of preferred embodiments in conjunction with the appended sheets of drawings, of which.

DETAILED DESCRIPTION OF A PRESENTLY PREFERRED EXEMPLARY EMBODIMENT

Figure 1:
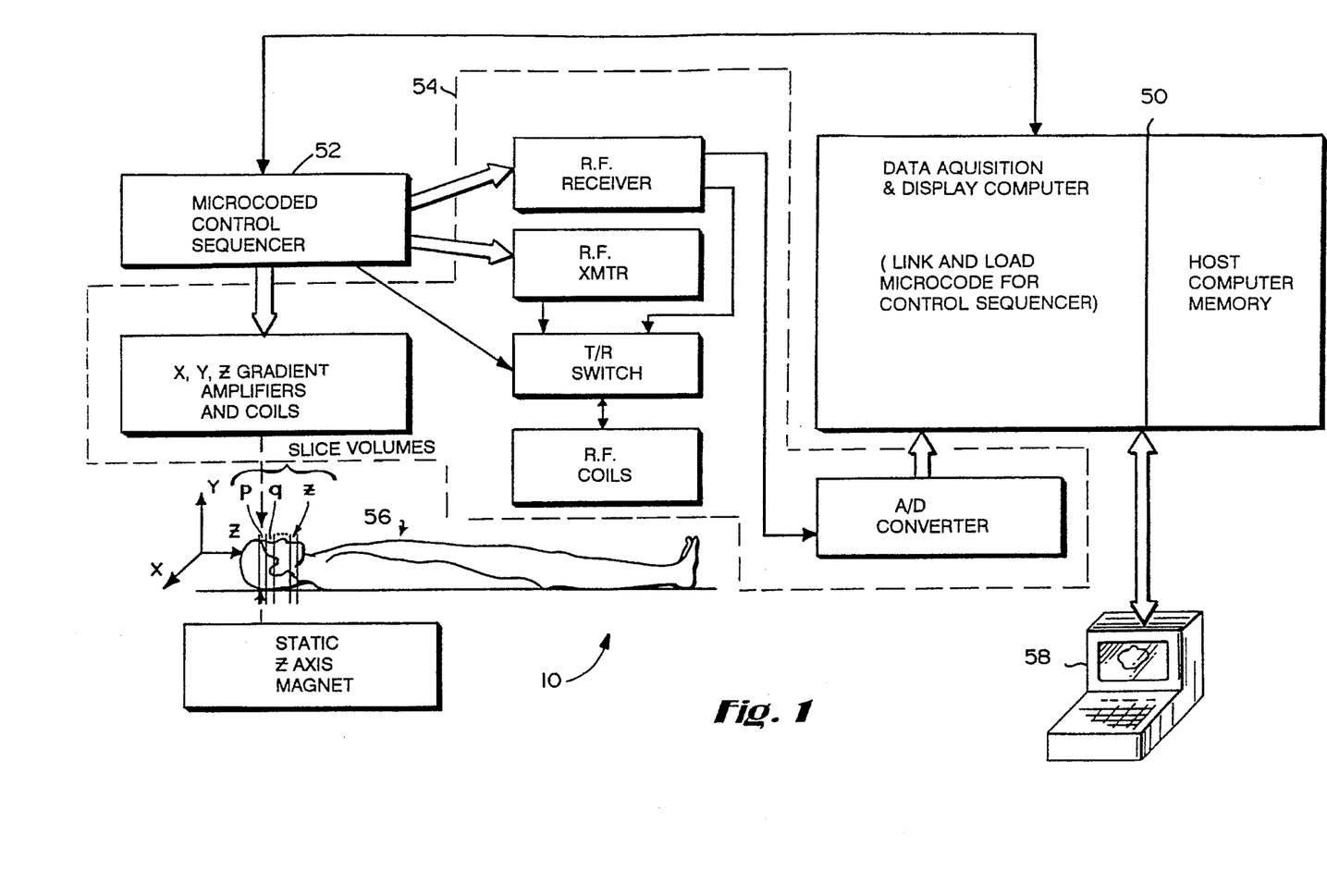
FIG. 1 is a schematic block diagram of an exemplary MRI system including a linker/loader apparatus and a real time sequencer/controller.

FIG. 1 is a schematic block diagram of an exemplary magnetic resonance imaging ("MRI") system 10 of the type that may advantageously be used in conjunction with the linker provided by the presently preferred exemplary embodiment of this invention. System 10 includes a computer 50, a sequencer 52, and an MRI subsystem 54. Subsystem 54 is controlled in real time by sequencer 52 so as to generate magnetic and radio frequency fields in order to stimulate nuclear magnetic resonance ("NMR") phenomena in an object 56 (e.g., a human body) to be imaged. A resulting image of body 56 on display 58 may show features and structures that cannot be seen using X-ray, ultrasound or other medical imaging techniques.

The basic techniques for magnetic resonance imaging are very well known and accordingly need not be explained here in detail. Very simply, MRI subsystem 54 generates a magnetic field which has the effect of aligning the spin axes of nuclei (e.g., hydrogen atom protons) within object 56. Radio frequency fields are then generated and applied to the body. These RF fields stimulate the nuclei to cause (temporary) realignment of their spin axes. Relaxation phenomena cause the nuclei to return to non or less stimulated states. As the nuclei return to such non or less stimulated states, they induce voltage into an RF coil that is received and detected by subsystem 54. Magnetic field gradients, phase encoding, and other techniques may be used to allow subsystem 54 to determine correspondence between received signals and location of the excited nuclei within the body. The received signals are processed using inverse Fourier transformation and other complex processings in order to generate an image of body 56.

As is well known, sequencer 52 is used to provide real time control over MRI subsystem 54 so that the subsystem generates appropriate fields at appropriate times, activates its receiver at appropriate times, etc. Sequencer 52 is preferably a dedicated hardware based microcoded sequencer including an internal random access memory program store for storing linked object (executable) code. The executable code is generated by computer 50 in response to commands inputted by a human operator via display/keyboard 58 (or a different display/keyboard workstation). More particularly, computer 50 executes a linker process (to be described in greater detail below) that accepts "link commands" (i.e., "source code" statements authored by a human being) and, in response, generates executable microcode for loading into the program store of sequencer 52.

Sequencer 52 then controls all of the real time events associated with MRI subsystem 54 under the control of the microcode generated by the linker. For example, sequencer 52 controls the generation of time and spatially varying fields, e.g., a radio frequency field having a time and spatially varying magnetic component. In MRI, the useful aspect of the radio frequency field is its magnetic component. The sequence of states provided by sequencer 52 is typically used to cause the generated field to vary in time. The main other aspect is that a controlled field is spatially varying. This includes changing from a uniform field to having a gradient turned on, or the reverse order of events. The spatial variation can be of the static or RF fields. Such fields are generated in various ways including, for example, repetitively generating RF pulses at times controlled by an interpulse repetition time TR and/or spin-echo time parameter TE. If the static field is low enough, the radio frequency may be so low that it is not radio frequency any more. In the 0.5 Gauss Earth's magnetic field, the Larmor frequency is only 2 kHz. There are also techniques where no gradient of the static field is used (all localization is by RF field gradients).

The preferred embodiment "link commands" contain program segments/procedures embedded in a loop syntax with loop index symbols and their ranges. Sequence parameters are in tables or other storage buffers which are indexed with one or more of the loop index symbol values as specified when they are created. For example, a table for the phase encoding gradient could be indexed by one loop index symbol to select an output value for each iteration of the loop; or it could be indexed by two loop index symbols if it were declared to be two dimensional (one to select a row and the other to select a column of the table). It is also possible to use formulas dependent on the loop index symbols and other constants and variables (either global or passed by value or reference) to represent a control parameter field in a particular instruction.

FIGS. 2A–2D together show a flowchart of exemplary program control steps performed by a preferred embodiment exemplary linker/loader process (hereafter "linker") provided by the present invention. In the preferred embodiment, the linker process is performed by computer 50, which generates executable microcode from pre-existing program segment object code and parameter values in response to link commands, loads the microcode into sequencer 52, and starts the sequencer so as to control MRI subsystem 54 to generate sequences of MRI events in real time. If the MRI Sequencer has paged microcode memory, the linker continues to generate and load microcode until the link command is completed.

Figure 2A:
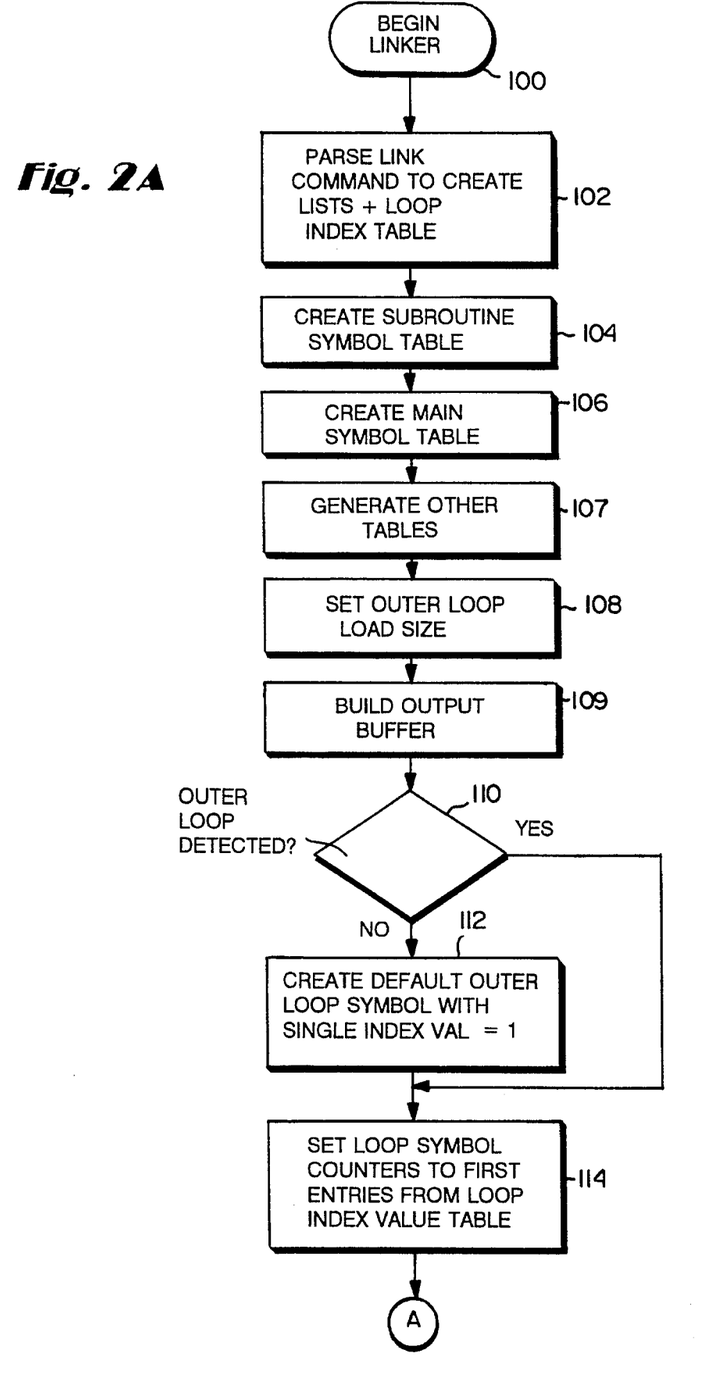
FIGS. 2A–2D are together a flowchart of exemplary program control steps performed by a preferred embodiment linker/loader.

Upon starting the linker (block 100), computer 50 gets the link commands from an input buffer and parses them for the purpose of creating a SubroutineList table, a MainList table and a LoopIndexValue table (block 102). The SubroutineList and the MainList include entries for loop symbols and loop scopes over program segments ("PSEGs") and other loops. The LoopIndexValue tables 200 so created contain entries for each loop index symbol value.

Figure 3:
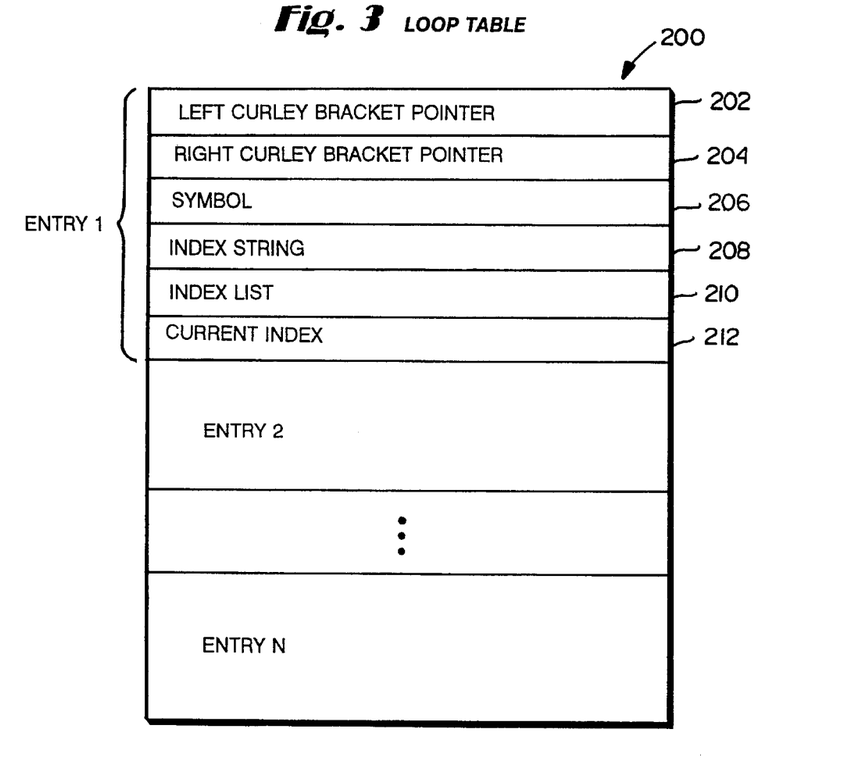
FIG. 3 is a schematic diagram of an exemplary loop table.

In somewhat more detail, block 102 first finds all inner loops by identifying the index into the command of each left and right curly-brackets. Block 102 also checks syntax to determine that all curly-brackets are in pairs. Block 102 then builds loop table 200 composed of plural entries, one for each loop symbol. As shown in FIG. 3, each entry of loop table 200 includes the following exemplary fields:

a left curly bracket pointer 202;

a right curly bracket pointer 204;

a symbol field 206 (this field preferably contains the name of the loop symbol);

an index string 208 (which may be of variable length and may contain a loop scope and/or range specifier);

an index list 210; and a current index field 212.

The following is exemplary pseudo-code for defining an exemplary entry of loop table 200:

```
typedef struct lp_tbl_entry
    {
        char *lcurbrk_ptr;
        char *rcurbrk_ptr;
        char symbol;
        char index_str[INDEX_STR_LEN];
        int index_list[INDEX_LIST_LEN];
        int curr_index;
    };
```

FIG. 2A block 102 also, as part of syntax checking, terminates each sub-string of the command with a null. In the preferred embodiment syntax, each sub-string begins at one of the following:

a left curly bracket;

the end of an index string;

the beginning of the link/load command; or the beginning of the main program segment portion of the link/load command.

Each sub-string in the preferred embodiment syntax ends at one of the following:

a left curly bracket; or a right curly bracket; or the end of the subroutine program segment portion of the link/load command; or the end of the main segment portion of the command.

Block 102 also, as mentioned above, creates a subroutine list table and a main list table. In the preferred embodiment this is done by parsing the link/load command into such tables with entries containing pointers to the loop table 200 which indicate the beginning and end of each loop. There will be two tables (one for main, one for subroutines) if there are subroutine program segments.

Block 102 also processes other parts of the link/load command into tables for use by the linker (i.e. level). In the preferred embodiment there is no cycle syntax since the outer loop takes over and generalizes the cycle syntax. Level retains its meaning of identifying a collection of parameter tables in the manner of the z-axis of a 3D spreadsheet.

Once block 102 has been executed, then blocks 104 and 106 are performed to create a subroutine symbol table and a main symbol table, respectively. Block 104 creates the SubroutineSymbol table with loop indexed line label symbols being expanded and entered once for each entry in each Loop table 200 (and block 106 performs a similar operation with respect to the main program segments). Since all link command loops are "unrolled" into sequential instructions, each line label symbol has an expanded internal representation corresponding to each of the loop index values specified for that line. Each line symbol in the subroutine symbol table has an associated absolute address. Block 104 saves the last absolute address. Each symbol in the main symbol table has an associated relative address with respect to the first main program segment instruction.

Figure 4:
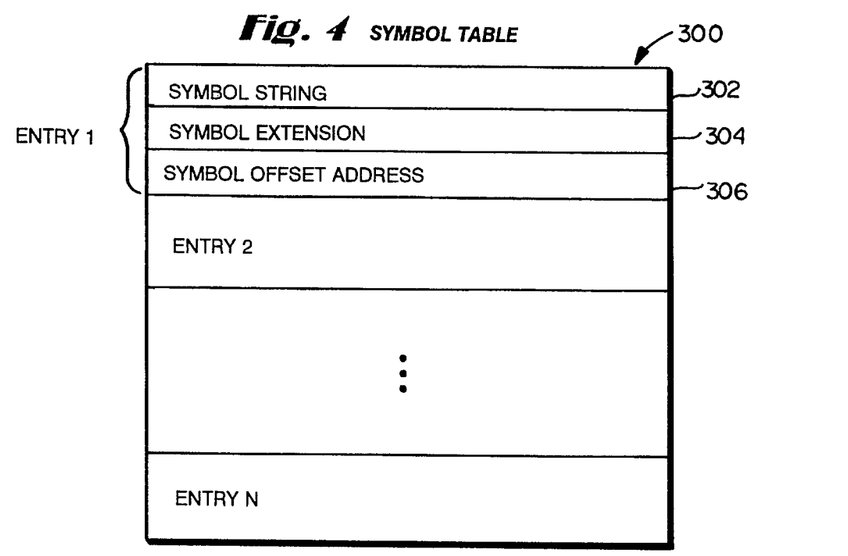
FIG. 4 is a schematic diagram of an exemplary symbol table.

FIG. 4 schematically shows exemplary structure/fields for the subroutine and main symbol tables (the subroutine symbol table 300 is shown, but in the preferred embodiment the main symbol table is identical in structure). Each entry in the preferred symbol table 300 includes a line label symbol string element 302, a symbol extension element 304, and a symbol address offset 306. Exemplary pseudocode for specifying symbol table 300 structure follows:

```
typedef struct sym_tbl_entry
    {
        {
        char sym_str[SYM_STR_LEN];
        int sym_exten[SYM_EXTEN_LEN];
        int sym_addr_offset;
        };
```

The sym_exten element 304 in the preferred embodiment is an array comprising the current collection of loop indices being used, and is constructed to have a specific set of active entries dependent on the actual loops within which the line label symbol is embedded in the program segment. Thus, the first entry in the sym_exten array 304 for each symbol corresponds to the outer loop and each entry thereafter to the next inner loop. The set of entries will always begin at sym_exten[0] in the preferred embodiment since there is always an outermost loop (it may be implicit) enclosing the subroutine and main parts of the link/load command. There may only be one index value declared for this loop. There is a copy of the symbol with the appropriate extension in the table for each permutation of possible loop symbol index values. As a result, it is necessary for subroutine loop symbols to have identical loop index values to the corresponding main loop symbols.

The linker then constructs any other tables associated with other fields of the link/load command (block 107), and sets the outer loop load size (block 108) as the number of main program segment instructions. The linker next builds, in memory, a load buffer for containing the linked code image (block 109), and begins the process of machine replicating program segment code for loading into the buffer.

Briefly, the linker performs the following function to machine replicate code:

use the link tables to set up the current sym_exten and look up a program segment or loop symbol;

get a program segment from the object code buffer;

locate jump symbols (corresponding to line label symbols) from this buffer with the current sym_exten in the symbol table and insert the absolute addresses in the microcode immediate address field; and identify parameter table and formula references and resolve them for the current sym_exten index value corresponding to associated loop symbol of that parameter table.

In more detail, the linker processes the linker SubroutineList or MainList entries one at a time, starting from the first (top) entry. If an outer loop is not detected (as indicated by the syntax rules described above) (decision block 110), then the outer loop is implicit and the linker creates a default outer LoopSymbol with a single index value equal to 1 (block 112). The linker then sets all LoopSymbol counters (pointers) to first entries in the LoopIndexValue tables 200 (block 114), and sets the address counter (used to address the output buffer) to the beginning of the buffer (block 116).

Figure 2B:
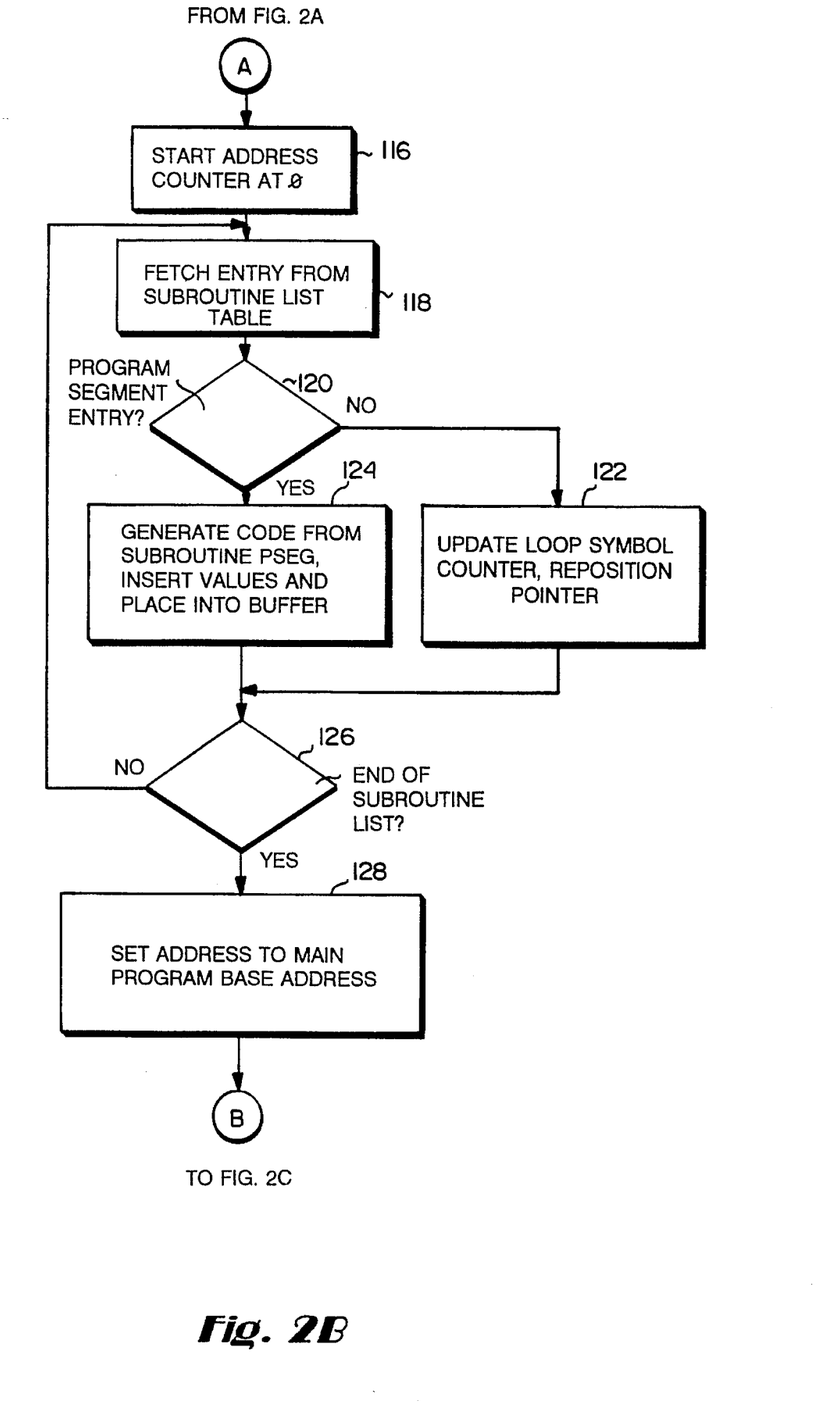

The linker next performs a loop (blocks 118–126) used to create the executable subroutine code. An entry from the SubroutineList table is fetched (block 118) and tested to determine whether it is a program segment entry (decision block 120).

If the entry is not a program segment entry ("N" exit of decision 120), the linker updates the indicated LoopSymbol counter and repositions the pointer to the next program segment or the next LoopSymbol entry in the SubroutineList table (block 122).

If the entry is a program segment entry ("Y" exit of decision 120), the linker loads lines of object code into the load buffer from the subroutine program segment buffer (block 124). In this process, block 124 inserts absolute addresses for line symbolic and indexed symbolic addresses (these addresses are obtained from the SubroutineSymbol table created by block 104), and also resolves references to parameter tables (PCTs) and formulas using the current value of the LoopSymbol counters and global variables. Block 124 increments the address counter after each line of code is inserted into the load buffer.

Figure 2C:
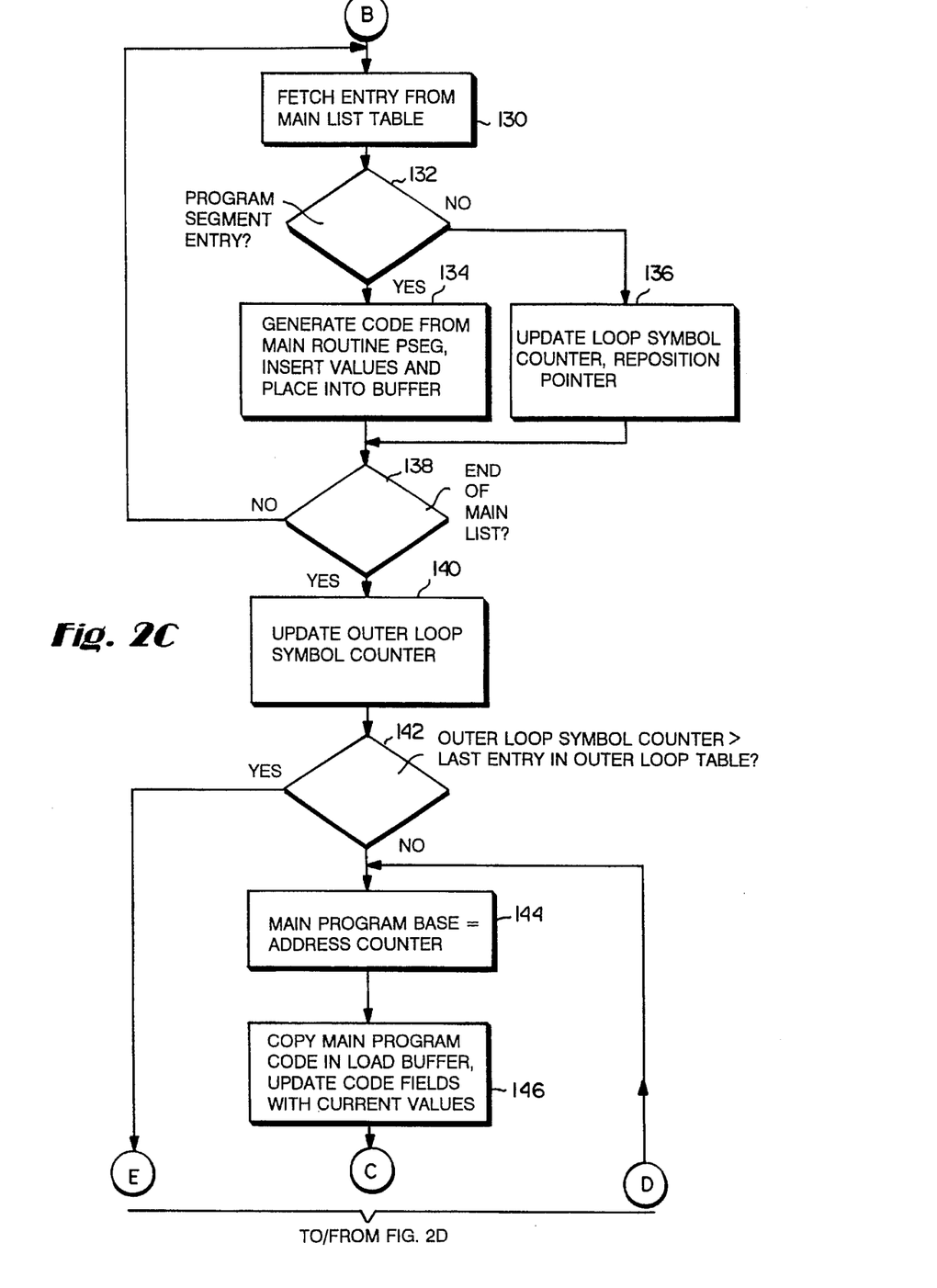

Decision block 126 determines whether the end of the SubroutineList has been reached (thereby indicating that all subroutine code has been generated). If the end of the list has not yet been reached, control returns to block 118 to fetch the next entry. If the end of the list has been reached, on the other hand, then the MainProgramBase address is set equal to the address counter (block 128) and the loop of blocks 130–138 is executed in order to generate main program segment executable code.

Block 130 fetches the next entry from the MainList table, and this entry is checked to determine whether it is a program segment entry (decision block 132).

If the entry is not a program segment entry ("N" exit of block 132), the linker updates the indicated LoopSymbol counter and repositions the pointer to the next program segment or the next LoopSymbol entry in the MainList table (block 136).

If the entry is a program segment entry ("Y" exit of block 132), the linker gets code from the main program segment buffer, inserts appropriate values, and loads the code into the output buffer (block 134). In more detail, the linker loads lines of object code from the main program segment buffer into the load buffer, in this process inserting absolute addresses for line label symbolic and indexed symbolic addresses (from the main symbol table) and resolving references to parameter tables and formulas using the current value of the LoopSymbol counters and global variables. Block 130 increments the address counter after each line of code is inserted into the load buffer. Block 130 also updates the OuterLoopReference table with entries for PCTs or equations associated with the outer LoopSymbol, including the current value of associated inner LoopSymbol counters.

Decision block 136 tests whether all of the MainList entries have been processed. If additional entries remain, then control returns to block 130 so as to fetch the next entry. If no additional entries remain, then control proceeds to block 140. Block 140 updates the outer LoopSymbol counter.

Figure 2D:
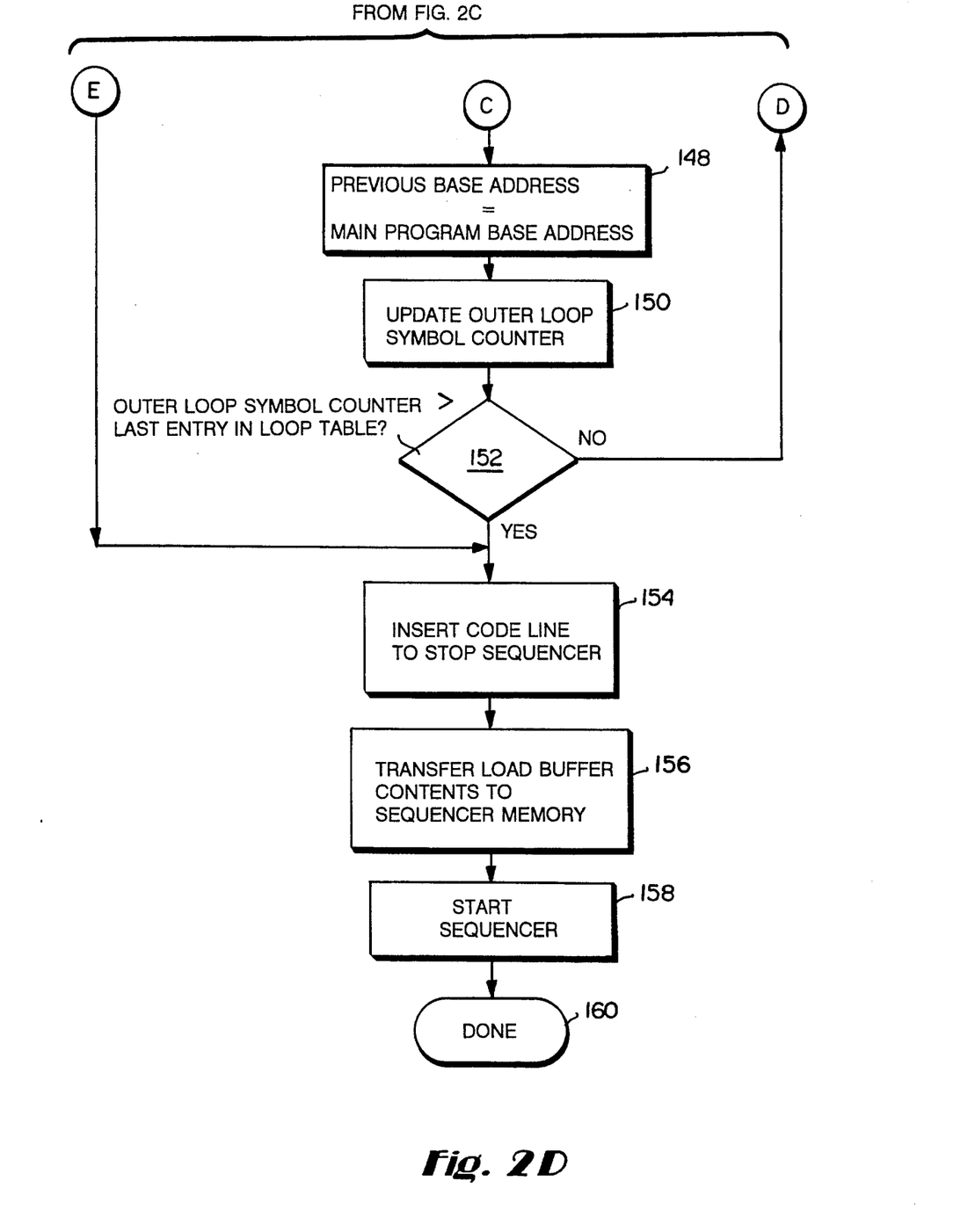

Decision block 142 then compares the updated LoopSymbol counter with the last entry in the outer LoopIndexValue table in order to determine whether there is more than one pass through the outer loop. If there is only one pass, then control is transferred to block 154 et seq. (to be discussed below). On the other hand, if the updated counter is less than the last entry in the outer LoopIndexValue table ("N" exit of decision block 142), steps 144–152 are performed to copy previously generated code within the load buffer (but inserting different values as appropriate) in order to replicate code for additional iteration(s) of the outer loop. In more detail, the MainProgramBase address is set to the value of the address counter (block 144). Block 146 then copies code in the load buffer starting at the previous base address to the next sequential locations in the load buffer starting at MainProgramBase address. The MainProgramBase address is used to determine and correct the offset to add to each address in the code lines as they are copied. The OuterLoopReference table is used to identify code fields which must be updated using the current value of the outer LoopSymbol counter to resolve PCT and formula references. The address counter is updated after each line is copied. Finally, the PreviousBase address is set to the MainProgramBase address (block 148), and the outer LoopSymbol counter is updated (block 150).

Next, decision block 152 determines whether all iterations of the outer loop have been completed by comparing the outer LoopSymbol counter with the last entry in the outer LoopIndexValue table. If additional iterations remain, then blocks 144–152 are repeated. If no additional iterations remain, then the linker has generated all required executable code. At this point, the linker inserts a halt instruction in the next sequential location of the load buffer so as to stop the sequencer (block 154), transfers the load buffer contents to the sequencer memory (block 156), and starts sequencer 52.

As will be understood by those skilled in the art, executable code may be generated in multiple segments for loading into paged microcode memory (see my copending application Ser. No. 07/579,631 atty. docket no. 89-179), or into a FIFO fed execution/interpretation buffer.

EXAMPLES

Example 1

An example of one possible linker syntax with nested loops is:

```
{START( )
    {SUBR1( )
     SUBR2( )
    }B 1:10>77,4
 SUBR3
/
 MAIN1( )
    {MAIN2( )
     MAIN3( )
    }B 1:10>77,4
 MAIN4( )
}A 1:256;LEVEL=2
```

In this example there are copies of the subroutines with the same A and B indices corresponding to copies of the main routines with the same loop symbol index values. This will result in the subroutine line symbols for each loop index value having the same symbol extensions as the referencing jump symbols in the main routines. These subroutines are thus callable from the corresponding main routines with the same loop symbol index values. Unique symbols at an outer nesting level may be referenced from within an inner loop since the index value of the inner loop symbol is not applied if the line symbol can be found in an outer loop (it cannot occur in an inner loop). The loop index symbol values are also used to resolve references to parameter tables, buffers or formulas dependent on a loop symbol.

Example 2

The following is a further example of a typical link command fragment using an exemplary program segment MAIN2:

```
{START( )
    {SUBR1( )
    }B 1:2>77,4
 SUBR2
/
    {MAIN1( )
    }B 1:2>77,4
 MAIN2( )
}A 1;LEVEL=2
```

An example of a program segment MAIN1 as it appears for LEVEL 2 is as follows:

| | | |
|---|---|---|
| z_rfon: | CONT | 5 msec y=T42 x=960 waveform=6 rf=on txsw=on |
| | CONT | T20 |
| | JSR sample | 2 usec |
| | CONT | 24 msec |

Note that in this program fragment the CONT instruction continues to the next instruction, JSR jumps to subroutine 'sample' T42 is a reference to a table of y-axis gradient values dependent on loop symbol A, and T20 is a table of clock values dependent loop symbol B. These values are as they are specified only for LEVEL 2 and could be different for another LEVEL, although the line label symbol, instructions and jump symbol would not change. Such a program database can be best thought of as a 3D computer spreadsheet where each instruction is a row of the spreadsheet and each field of the instruction is a column for example. Only the non-default valued fields are shown in this example. The LEVEL then corresponds to the third dimension of the spreadsheet, one level of which appears at a time on a display screen or in any given edit window on the display screen.

The following is an example of a loop table 200 for the exemplary program fragment set forth above using the MAIN1 program segment:

```
lp_tbl_entry[0]
    {
    lcurbrk_ptr =      0
    rcurbrk_ptr =      59
    symbol =           A
    index_str[ ] =     1
    index_list[ ] =    encoded array
    curr_index =
    }
lp_tbl_entry[1]
    {
    lcurbrk_ptr =      8
    rcurbrk_ptr =      16
    symbol =           B
    index_str[ ] =     1:2>77,4
    index_list[ ] =    encoded array
    curr_index =
    }
lp_tbl_entry[2]
    {
    lcurbrk_ptr =      33
    rcurbrk_ptr =      41
    symbol =           B
    index_str[ ] =     1:2>77,4
    index_list[ ] =    encoded array
    curr_index =
    }
```

The following is an example of a corresponding link table:

| entry number | |
|---|---|
| 0 | pointer to lp_tbl_entry[0] |
| 1 | pointer to START( ) |
| 2 | pointer to lp_tbl_entry[1] |
| 3 | pointer to SUBR1( ) |
| 4 | pointer to lp_tbl_entry[1] |
| 5 | pointer to SUBR2 |
| 6 | token indicating end of subroutines |
| 7 | pointer to MAIN1( ) |
| 8 | pointer to lp_tbl_entry[2] |
| 9 | pointer to MAIN2( ) |
| 10 | pointer to lp_tbl_entry[2] |
| 11 | pointer to MAIN3( ) |
| 12 | pointer to lp_tbl-entry[0] |

The following is an example of a fragment of a corresponding symbol table 300:

```
        .
        .
        .
    sym_tbl_entry
        {
        sym_str = z_rfon
        sym_exten[0] = 1
        sym_exten[1] = 77
        sym_addr_offset = . . .
        }
        .
        .
        .
    sym_tbl_entry
        {
        sym_str = z_rfon
        sym_exten[0] = 1
        sym_exten[1] = 81
        sym_addr_offset = . . .
        }
        .
        .
        .
```

Example 3

The following is an example of a link command used for 3D inner volume imaging:

| Command | Comments |
|---|---|
| {{Start | : jump to 1st instruction |
| {{3Dsub1(TE=28m,TR=1) | : subroutine with time |
| 3dsub2($2avg,P0=90,P1=270)}S1>61}J91 | : subroutine with 2 average |
| | :   macro argument and RF phases |
| 3Dsample(args)/ | : subroutine for sampling |
| {{3Dmain(args)}S1>61}J91 | : main routine for inner volume with |
| | :   delta F for the 180 degree RF pulse |
| | :   in J-type PCT |
| Navg($2avg) | : multiple average function with |
| | :   a macro argument for 2 averages |
| }C65:192/N4 | : 128 cycles with 4 spin conditioning |

| Command | Comments |
| --- | --- |
| | : cycles at the beginning of a load |
| }D1:8; | : 8 3D longitudinal phase encodings |
| L1. | : level 1 PCTs |

Note that this link command allows for a continuum of TR and TE values through the arguments supplied to the basic sequence functions combined to create the final sequence. The argument for the number of averages is preceded by a '$' to indicate the selection of a macro within the procedure in which it appears having the desired code for the number of averages indicated. Note that a macro is a block of microcode instructions inserted in a specific location within a program segment. When the macro label is passed as an argument to a procedure, the instructions are included. More than one macro label may be used at a specific location in the segment.

The one-to-one relationship between the code specified by the link command and that loaded into the sequencer memory provides a straightforward verification and debugging tool for the hardware.

Example 4

The above example illustrates the possibility of having a few procedures for single-slice template sequences supporting all spin echo or all partial flip or all 3D imaging protocols. Another example of this type of capability is the following spin echo sequence:

| | |
| --- | --- |
| {Start | : jump to 1st instruction |
| {SEsub1(TE=28m,TR=0.5) | : subroutine with time |
| | :  and RF phase arguments |
| SEsub2($2avg,P0=0,P1=90)}S1:20>61,4 | : subroutine with 2 average |
| | :  macro argument and RF |
| SEsample(args)/ | : sampling subroutine |
| {SEmain(args)}S1:20>61,4 | : main routine for spin echoes |
| Navg($2avg) | : multiple average function with |
| | :  a macro argument for 2 averages |
| {C1:256/N2; | : 256 cycles with 2 spin conditioning |
| | :  cycles at the beginning of a load |
| L1. | : level 1 PCTs |

Note that in this sequence, as in Examples 2 and 3, there is no main program segment required to provide a jump destination from the Start program segment containing a CONT instruction into the main "S" loop. This is due to an extension of the rules for use of special symbols beginning with X, Y or Z. These symbols are currently used to support a jump to the SEsample subroutine from within the subroutine "S" loop since they are not replicated with a loop index value extension inside a loop as are all other line symbols. The new rule allows use of these symbols as entry points to inner loops (if they have not already been encountered by the linker in previous segments). Any recurrence of this symbol other than at the first instruction where it is used in the "S" loop as an entry line symbol results in an error. Thus only one instance of the entry symbol is found in the symbol table for the first slice in the main "S" loop and Start can jump to it directly, saving a main routine instruction and reducing the number of reloads of the Sequencer memory.

Example 5

Since two so-called "spoiler" irradiations may be required to spoil flow related signal both above and below a set of slices generated using offset delta F PCTs, it is possible to use a "K" loop specification and K-type PCT to be used in conjunction with the "J" loop in the link command. An example of this construct for spin echoes is as follows:

| | |
| --- | --- |
| {Start | : jump to 1st instruction |
| {{{Spoil1 | : first spoiler |
| SEsub1(TR=1,TE=30m,P0=90) | : subroutine |
| SEsub2($1avg) | : subroutine |
| Spoil2}SA1:10>61,2}J31}K54 | : second spoiler and J and K |
| | :  indices for spoiler positioning |
| SEsample(args)/ | : sample subroutine |
| {{{SEmain(args)}SA1:10>61,2}J31}K54 | : main function |
| Navg($2avg) | : multiple average function with |
| | :  a macro argument for 2 averages |
| }C1:256/N2; | : 256 cycles with 2 spin conditioning |
| | :  cycles at the beginning of a load |
| L2. | : level 2 PCTs |

ALTERNATE EMBODIMENTS

The MRI sequencer implementation underlying the FIG. 2A–2D flowchart is considered to be preferred. However, the principles provided by the present invention may be used to advantage with a number of different sequencer architectures so as to provide process(es) (which are not necessarily equivalent to our preferred process). For example, one common type of MRI sequencer architecture, which is used by Toshiba, utilizes more hardware to reduce the amount of software needed to run a sequence. The control parameters which change within the main program template are loaded into FIFOs or ring buffers and outputted under control of the MRI sequencer as it executes the main program.

To accommodate such sequencer hardware, the linker shown in FIGS. 2A–2D could be changed such that only a single copy of the main program microcode would be used to implement all link command loops (e.g., at least block 146 would be eliminated and blocks 142–144, 148–152 would be modified). The resulting single copy code template would be encoded with strobe outputs from the control fields which change during execution so as to cause the correct value to be present at the output of the FIFO or ring buffer for that parameter after each line of code is executed. Software then could be used to compute values and load them into the FIFOs/ring buffers of sequencer 52 before the sequencer begins execution and/or while execution is in progress (hardware with lists/FIFOs may require separate and/or delayed parameter generation to be supplied by the host after the executable code is running/being interpreted due to their limited size). Inner loops of the link command (as distinct from hardware inner loops that are possible in the preferred embodiment disclosed above) could be expanded into in-line code as in the preferred embodiment, or could be supported by hardware execution. The outer loop would be supported by hardware and would be executed as many times as specified for the outer loop index symbol.

If the executable image has only immediate data for internal instruction sequencing and for output control fields as the worst case, then copies of all code segments for all index values associated with all loop variables must be created and placed in the image buffer (as described in connection with the main embodiment shown in FIGS. 2A–2D). However, if the hardware supports indexed hardware parameter lists in random access memory registers for external control parameter fields, then a reduced image could be built with appropriate control of the hardware resources for producing the output control fields selected by the loop variable indices. On the other hand, if the hardware supports indexed lists or FIFOs for parameter control fields, then an index/FIFO demand value can be placed in that microcode field. If the hardware supports arithmetic logic units and registers for incrementally computing the parameter value of a control field, then the register ID and increment/decrement control bits may be placed into the microcode field. It is implicit in all the above cases that the preferred precise simultaneous output timing of all control fields is strictly maintained during sequence execution. Also, it is preferred that all instruction time durations must be to the accuracy of the system clock.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. In a magnetic resonance imaging (MRI) system having a sequencer which controls generation of at least one of (1) a spatially varying magnetic field, and (2) a spatially varying RF field, the system further including a linking computer coupled to the sequencer the linking computer linking code to provide linked executable code for execution by the sequencer, a method for linking code for loading into and execution by the sequencer, said method including:

linking code on a linking computer by performing at least the following steps:
   (a) providing, on the host computer, at least one link loop definition associated with plural sets of parameter values, and
   (b) generating, with the linking computer, linked executable code in response to said link loop definition and said plural sets of parameter values;
   (c) loading the linked code from the linking computer into said sequencer;
   (d) executing said provided linked code with said sequencer; and
   (e) controlling at least one of (1) a spatially varying magnetic field, and (2) a spatially varying RF field in accordance with said sequencer execution.

2. A method as in claim 1 wherein said generating step (b) includes substituting at least one of said plural parameter value sets into previously generated code.

3. A method as in claim 1 wherein program instructions specify N iterations of said link loop, N an arbitrary integer, and wherein said generating step (b) includes generating N copies of inline code to said sequencer, each of said N copies including substitute values obtained from said plural sets of parameter values.

4. A method as in claim 1 further including requiring explicit specification of the range and/or scope of said link loop.

5. A method as in claim 4 further including the step of automatically checking to determine whether said range and/or scope specification is present.

6. A method as in claim 1 further including specifying, as part of said link loop definition, that said link loop is nested with at least one other link loop.

7. A method as in claim 1 further including specifying, as part of said link loop definition, that said link loop is nested with K other link loops, K an arbitrary integer.

8. A method as in claim 1 wherein:
   said method further includes defining a further loop for execution by said sequencer; and
   said generating step includes generating code in response to said defined further loop; and
   said executing step comprising iteratively executing said further loop representing code with said sequencer.

9. A method as in claim 1 further including defining global symbolic function arguments within said link loop definition.

10. A method as in claim 1 further including displaying at least a part of said link loop definition in a multidimensional spreadsheet format.

11. A method as in claim 1 further including specifying a value specified by a formula.

12. A method as in claim 1 further including referencing a first set of parameter values with a second set of parameter values different from said first set.

13. A system for generating executable code for a sequencer of a magnetic resonance imaging (MRI) system, said system including:

a linking computer for linking code to provide linked code, the linking computer including:

link associating means for associating at least one link loop definition with at least one set of parameter values and at least one scope and/or range parameter, linking means coupled to the linking associating means for generating linked executable code in response to said link loop definition, said parameter values set, and said scope and/or range parameter, and loading means coupled to the linking means for providing said generated linked executable code to said sequencer; and a sequencer coupled to the linking computer, the sequencer executing said provided linked executable code so as to provide a controlled sequence of states defining at least one of (i) a magnetic field, and (ii) a radio frequency field.

14. A system as in claim 13 wherein said generating and providing means includes means for generating and providing a plurality of copies of inline code to said sequencer, the number of iterations being specified at least in part by said range and/or scope parameter, each of said iterations including substitute values obtained from said sets of parameter values.

15. A system as in claim 13 further including means for requiring explicit specification of the range and/or scope parameter.

16. A system as in claim 13 further including means for automatically checking to determine whether said range and/or scope parameter has been specified.

17. A system as in claim 13 wherein said link loop definition specifies nesting within at least one other link loop.

18. A system as in claim 13 wherein said link loop definition specifies nesting within K other link loops, K an integer.

19. A system as in claim 13 wherein:

said system further includes means for defining a further loop for execution by said sequencer;

said generating and providing means includes means for providing code representing said further loop; and said sequencer iteratively executes said provided code representing said further loop.

20. A system as in claim 13 further including means for defining global symbolic function arguments associated with said link loop definition.

21. A system as in claim 13 further including means for displaying at least a part of said link loop definition in a multidimensional spreadsheet format.

22. A system as in claim 13 further including means for specifying a formula associated with said link loop.

23. A system as in claim 13 further including means for referencing a further set of parameter values with said first-mentioned set of parameter values.

24. In a magnetic resonance imaging (MRI) system having a linking computer which links code to provide an executable linked code and provides the executable linked code to a sequencer which executes the linked code to control generation of at least one of a spatially varying magnetic field and a spatially yawing RF field, a method for linking code for execution by the sequencer, said method including:

programming the linking computer to:

(a) define at least one global variable;

(b) provide at least one link loop definition;

(c) generate linked executable code in response to said link loop definition and said defined global variable; and (d) provide said generated code to said sequencer and load said generated linked executable code into said sequencer;

(e) executing said provided linked executable code with said sequencer; and (f) controlling, with the sequencer, at least one of a spatially varying magnetic field and a spatially varying RF field in accordance with said execution.

25. A system as in claim 24 wherein said defining step (a) comprises defining a global system RF pulse repetition time (TR), and said generating step (c) includes the step of generating code parameters in accordance with said specified global RF pulse repetition time.

26. A method as in claim 25 wherein said generating step (c) further includes the step of changing slice-specific parameters in said code.

27. A system as in claim 24 wherein said defining step (a) comprises defining a global system spin-echo time parameter (TE), and said generating step (c) includes generating code parameters in accordance with said global parameter TE.

28. In a magnetic resonance imaging (MRI) system having a linking computer that performs a linking operation to provide executable linked code for execution by a sequencer, the sequencer controlling generation of at least one of a spatially varying magnetic field and a spatially varying RF field in accordance with the linked executable code, a method including:

linking code on the linking computer, including:

(a) providing at least one link loop definition specifying plural sets of parameter values;

(b) defining plural nested loops at the link level, including specifying a loop index symbol for said loop and specifying at least one range and/or scope parameter associated with said index symbol;

(c) associating each of said plural defined nested loops with a different one of said plural sets of parameter values; and (d) generating linked, executable sequencer code in response to said defined nested loops, said plural parameter value sets and said range and/or scope parameter, including the step of determining whether a link loop associated with a particular MRI parameter is defined by a link loop definition and specifying at least one default value for said parameter if said determination reveals that no such definition exists;

(e) loading the linked executable code from the linking computer into the sequencer; and (f) executing said loaded code with said sequencer to generate an ordered sequence of sequencer states, said ordered sequence controlling at least one of a spatially varying magnetic field and a spatially varying RF field.

* * * * *